(12) United States Patent
Shaltout et al.

(10) Patent No.: US 10,161,797 B2
(45) Date of Patent: Dec. 25, 2018

(54) SUB-MILLIMETER REAL-TIME CIRCULAR DICHROISM SPECTROMETER WITH METASURFACES

(71) Applicant: Purdue Research Foundation, West Lafayette, IN (US)

(72) Inventors: Amr Shaltout, West Lafayette, IN (US); Alexander Kildishev, West Lafayette, IN (US); Vladimir Shalaev, West Lafayette, IN (US); Jingjing Liu, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 160 days.

(21) Appl. No.: 15/202,048

(22) Filed: Jul. 5, 2016

(65) Prior Publication Data

US 2017/0003169 A1    Jan. 5, 2017

Related U.S. Application Data

(60) Provisional application No. 62/188,727, filed on Jul. 5, 2015.

(51) Int. Cl.
*G01J 3/447* (2006.01)
*G02B 1/00* (2006.01)
(Continued)

(52) U.S. Cl.
CPC ............ *G01J 3/447* (2013.01); *G01J 3/0224* (2013.01); *G01J 3/0256* (2013.01);
(Continued)

(58) Field of Classification Search
CPC ...... G01J 3/0224; G01J 3/0213; G01J 3/0216; G01J 3/0229; G01J 3/0245; G01J 3/0256;
(Continued)

(56) References Cited

U.S. PATENT DOCUMENTS 8,848,273 B2 *  9/2014  Yu ............................ G02F 1/01
                                                         359/238
2003/0218744 A1 * 11/2003  Shalaev ................ B82Y 10/00
                                                         356/301

(Continued)

FOREIGN PATENT DOCUMENTS

EP        3133385 A1 *  2/2017  ............ G01N 21/19
KR    101494326 B1 *  2/2015
(Continued)

OTHER PUBLICATIONS

Zhao, Yang et al., "Recent Advances on optical metasurfaces," 2014, Journal of Optics 16 123001, 14 pages.*

(Continued)

*Primary Examiner* — Gordon J Stock, Jr.
(74) *Attorney, Agent, or Firm* — Purdue Research Foundation

(57) ABSTRACT

A circular dichroism spectrometer which comprises a metasurface. The metasurface has a plurality of anisotropic antennas configured to simultaneously spatially separate LCP and RCP spectral components from an incoming light beam. An optical detector array is included which detects the LCP and RCP spectral components. A transparent medium is situated between the metasurface and the optical detector array.

21 Claims, 9 Drawing Sheets

(51) Int. Cl.
  *G01N 21/19* (2006.01)
  *G01J 3/02* (2006.01)
  *G01J 3/28* (2006.01)

(52) U.S. Cl.
  CPC ............ *G01J 3/2803* (2013.01); *G01N 21/19* (2013.01); *G02B 1/002* (2013.01)

(58) Field of Classification Search
  CPC .. G01J 3/2803; G01J 3/447; G01J 4/00; G01J 4/02; G01J 4/04; G01J 2004/002; G01J 2004/004; G01J 2004/005; G01J 2004/007; G01J 2004/008; G01N 21/19; G01N 21/21; G01N 2021/216; G02B 1/002; G02B 1/005; G02B 1/007
  See application file for complete search history.

(56) References Cited

U.S. PATENT DOCUMENTS

| | | | | |
|---|---|---|---|---|
| 2010/0232017 | A1* | 9/2010 | McCarthy | B82Y 20/00 359/485.05 |
| 2011/0261441 | A1* | 10/2011 | Zheludev | G02B 1/005 359/352 |
| 2012/0268818 | A1* | 10/2012 | Liu | G02B 1/002 359/494.01 |
| 2012/0280872 | A1* | 11/2012 | Werner | H01Q 15/0053 343/753 |
| 2014/0085693 | A1* | 3/2014 | Mosallaei | G02B 1/002 359/107 |
| 2015/0162658 | A1* | 6/2015 | Bowers | H01Q 15/006 342/385 |
| 2017/0030773 | A1* | 2/2017 | Han | G01J 3/0208 |
| 2017/0356843 | A1* | 12/2017 | Alu | G01N 21/554 |
| 2018/0066991 | A1* | 3/2018 | Mueller | G01J 4/02 |

FOREIGN PATENT DOCUMENTS

| | | | | |
|---|---|---|---|---|
| WO | WO 2008142723 A2 * | 11/2008 | | G01N 21/19 |
| WO | WO 2016000001 A1 * | 1/2016 | | G01J 4/00 |
| WO | WO 2016159880 A1 * | 10/2016 | | G02B 5/30 |

OTHER PUBLICATIONS

Yin, Xiaobo et al., "Photonic Spin Hall Effect at Metasurfaces," Mar. 22, 2013, Science, vol. 339, pp. 1405-1407.*

Cao, Tun et al., "Extrinsic 2D chirality: giant circular conversion dichroism from a metal-dielectric-metal square array," Dec. 11, 2014, Scientific Reports 4: 7442, pp. 1-7.*

* cited by examiner

SUB-MILLIMETER REAL-TIME CIRCULAR DICHROISM SPECTROMETER WITH METASURFACES

CROSS-REFERENCE TO RELATED APPLICATIONS

The present patent application is related to and claims the priority benefit of U.S. Provisional Patent Application Ser. No. 62/188,727, filed Jul. 5, 2015, the contents of which is hereby incorporated by reference in its entirety into the present disclosure.

STATEMENT REGARDING GOVERNMENT FUNDING

This invention was made with government support under W911NF-13-1-0226 awarded by the Army Research Office, FA9550-14-1-0389 awarded by the Air Force Office of Scientific Research; and 3002095871 awarded by the National Science Foundation. The government has certain rights in the invention

TECHNICAL FIELD

The present disclosure relates to nanophotonic devices, and more specifically, production of a circular dichroism spectrometer using nanophotonic techniques.

BACKGROUND

Circular Dichroism (CD) spectrometry is a very important tool in sensing chiral molecular structures which don't superimpose onto their mirror image. Chiral structures are very recurrent in biological media and organic compounds. Therefore, CD spectrometers find many applications in areas including, but not limited to, biological sensing, stereochemistry, crystallography and DNA structural analysis.

CD spectrometers measure the spectrum of differential absorption between left circularly polarized (LCP) light and right circularly polarized light (RCP). Conventional prior art CD spectrometers measure LCP and RCP spectra sequentially. The laser sources are tuned to generate LCP across the wavelength range and measure the absorption, and then, the source is switched to RCP and the process is repeated. The process is time consuming, and involves much complicated hardware to switch the polarization of the laser, thereby increasing the dimensions of the device.

Polarization gratings have been proposed to split LCP and RCP spatially. The gratings can be used to obtain real-time concurrent measurement of LCP and RCP spectra. This can eliminate the need to use complicated switchable sources. However, these polarization gratings require large thickness to accumulate optical phase delays between the major and minor axes of polarization gratings. Therefore, improvements are needed in the field.

SUMMARY

The present disclosure applies optical metasurface technology to perform spatial separation of LCP and RCP spectra using a single deeply subwavelength metasurface layer. The disclosed system can generate strong phase accumulation within a layer about 100 nm thick which can be used to reflect and\or transmit LCP and RCP efficiently in different sides at a wavelength dependent angle. As a result, the entire CD spectrometer device may be sub-millimeter in dimensions, including spatial separation of LCP and RCP spectra and collecting their measurements at a charge-couple device (CCD) array.

According to one embodiment, a miniature real-time CD spectrometer is disclosed which separates LCP and RCP spectra in space. A metasurface layer is used to efficiently split LCP and RCP spectra, and then, a CCD array is used to collect these spectra.

Separation of LCP and RCP spectra is performed either in transmission or reflection mode. For transmission mode, a dielectric metasurface is used, while for reflection mode, a plasmonic metasurface is used.

The metasurface and CCD layers are separated with a polymer or any other transparent medium. The whole spectrometer is sub-millimeter in 3D dimensions.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein.

DETAILED DESCRIPTION

Figure 1:
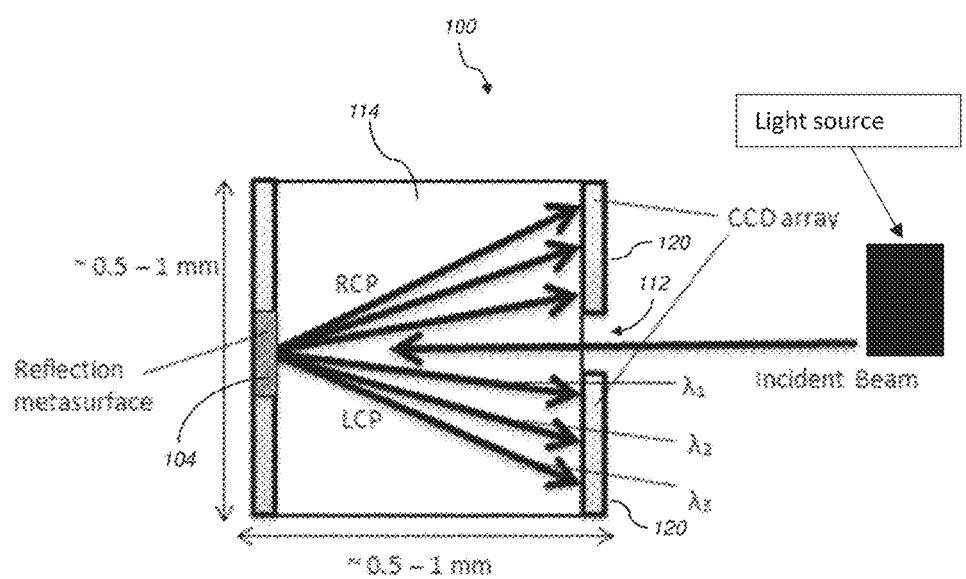
FIG. 1 shows a conceptual illustration of a CD spectrometer implemented using a reflective metasurface according to one embodiment.
Figure 2:
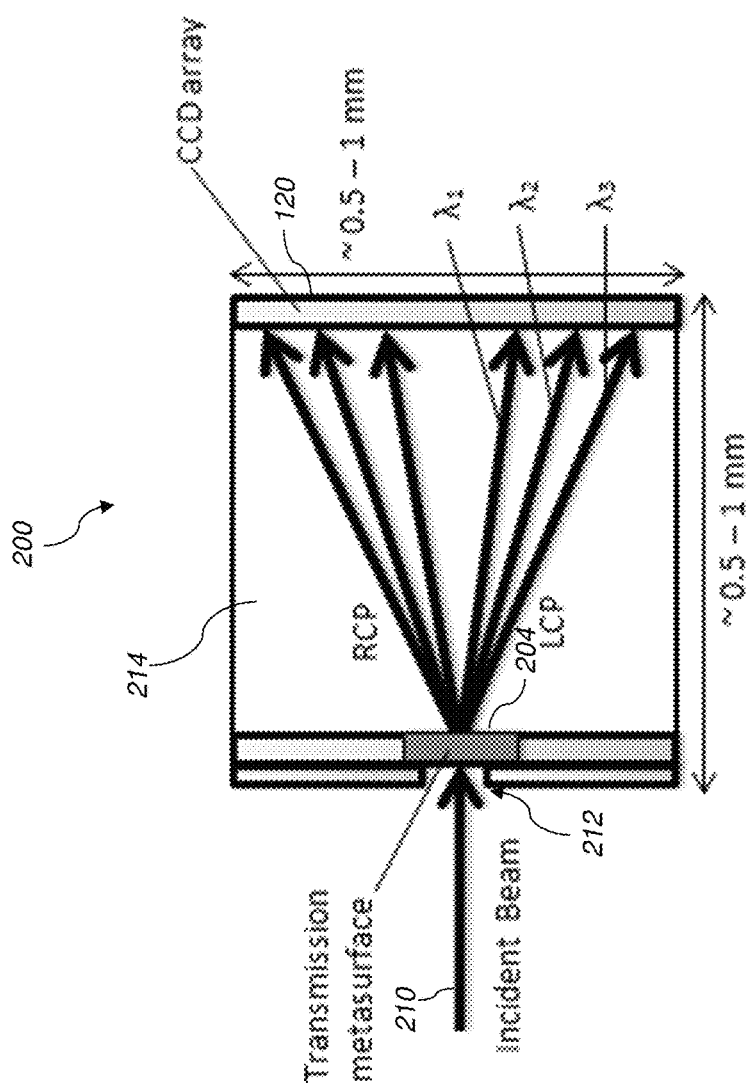
FIG. 2 shows a conceptual illustration of a CD spectrometer implemented using a transmission metasurface according to one embodiment.

The presently disclosed CD spectrometer is configured to be submillimeter in dimensions. FIGS. 1 and 2 show conceptual schematics of the whole CD spectrometer, where spectral components are being separated using reflection and transmission metasurfaces respectively. A key component of the spectrometer is the beam splitting metasurface. The metasurface spatially separates LCP and RCP spectra of the incident light. The incident light beam is of typical beam diameter ~50-500 μm. After the beam falls onto the reflection (or transmission) metasurface, LCP and RCP components are reflected (or transmitted) into opposite directions. In addition, each wavelength is reflected (or transmitted) at a different angle, thereby resolving the individual spectral components of the beam. As a result, the LCP and RCP components are completely separated in space.

The LCP and RCP spectral components are then projected onto an array of charged coupled detectors (CCD). A distance ~0.5-1 mm is required between the metasurface and CCD array layers for adequate separation of spectral components of light. For mechanical stability, this distance is filled with a transparent dielectric polymer or any other transparent material.

FIG. 1 shows a conceptual illustration of a CD spectrometer 100 implemented using a reflective metasurface 104 according to one embodiment. Each side of the spectrometer 100 is ~0.5-1 mm in length. A broadband light beam 110 enters the spectrometer through a hole 112 having a width of ~50-500 μm. The light goes through a transparent bulk medium 114, hitting the reflective metasurface 104. The metasurface 104 separates the spectral components of LCP and RCP as shown, and a CCD array 120 is used to detect the data from these separated components.

FIG. 2 shows a conceptual illustration of a CD spectrometer 200 implemented using a transmission metasurface 204. Each side of the spectrometer 200 is ~0.5-1 mm in length. A broadband light beam 210 enters the spectrometer 200 through a hole 212 having a width of ~50-400 μm and hits the transmission metasurface 204. The metasurface 204 separates the transmitted spectral components of LCP and RCP which go through a transparent bulk medium 214, and a CCD array 220 is used to detect the data from these separated components.

The most important part of the CD spectrometer is the beam splitting metasurface. The detailed structure of the reflecting metasurface is shown in FIGS. 3 and 4 and that of the transmission metasurface in FIG. 5.

Figures 3A, 3B:
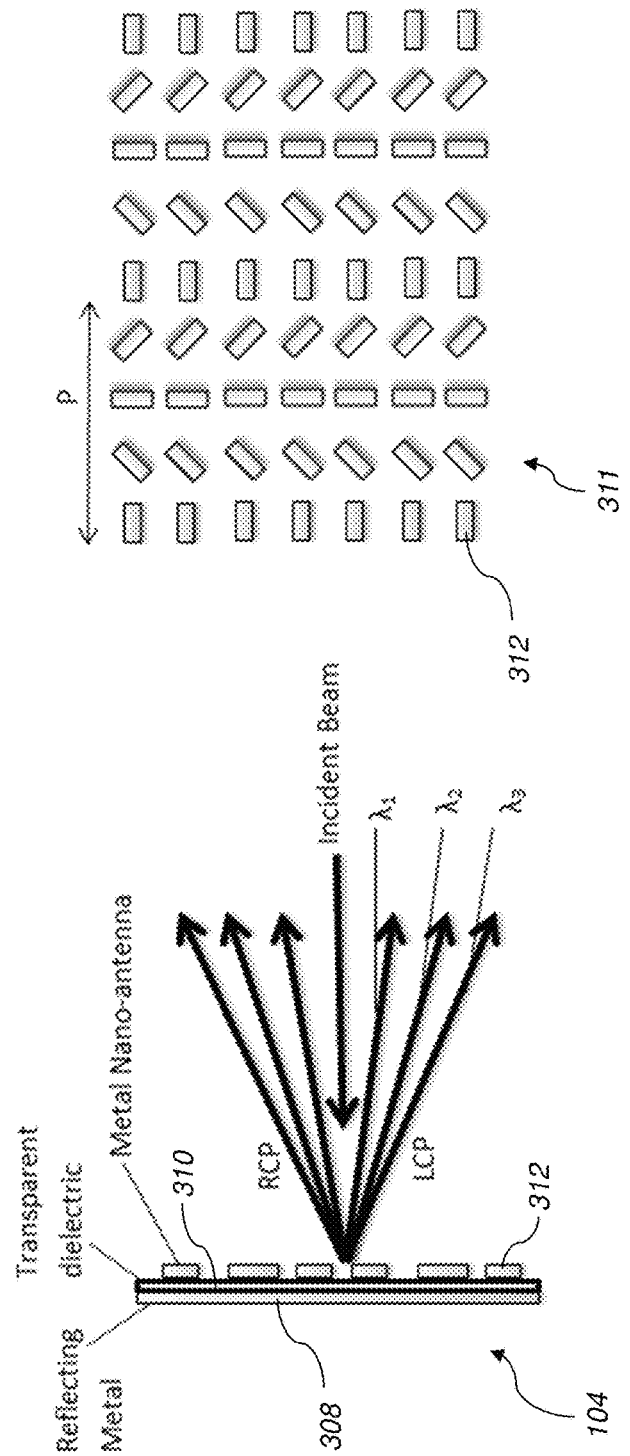
FIGS. 3(A) and 3(B) show the structure of the reflective metasurface of FIG. 1 from a cross-sectional view and top view, respectively, according to one embodiment.
Figure 4:
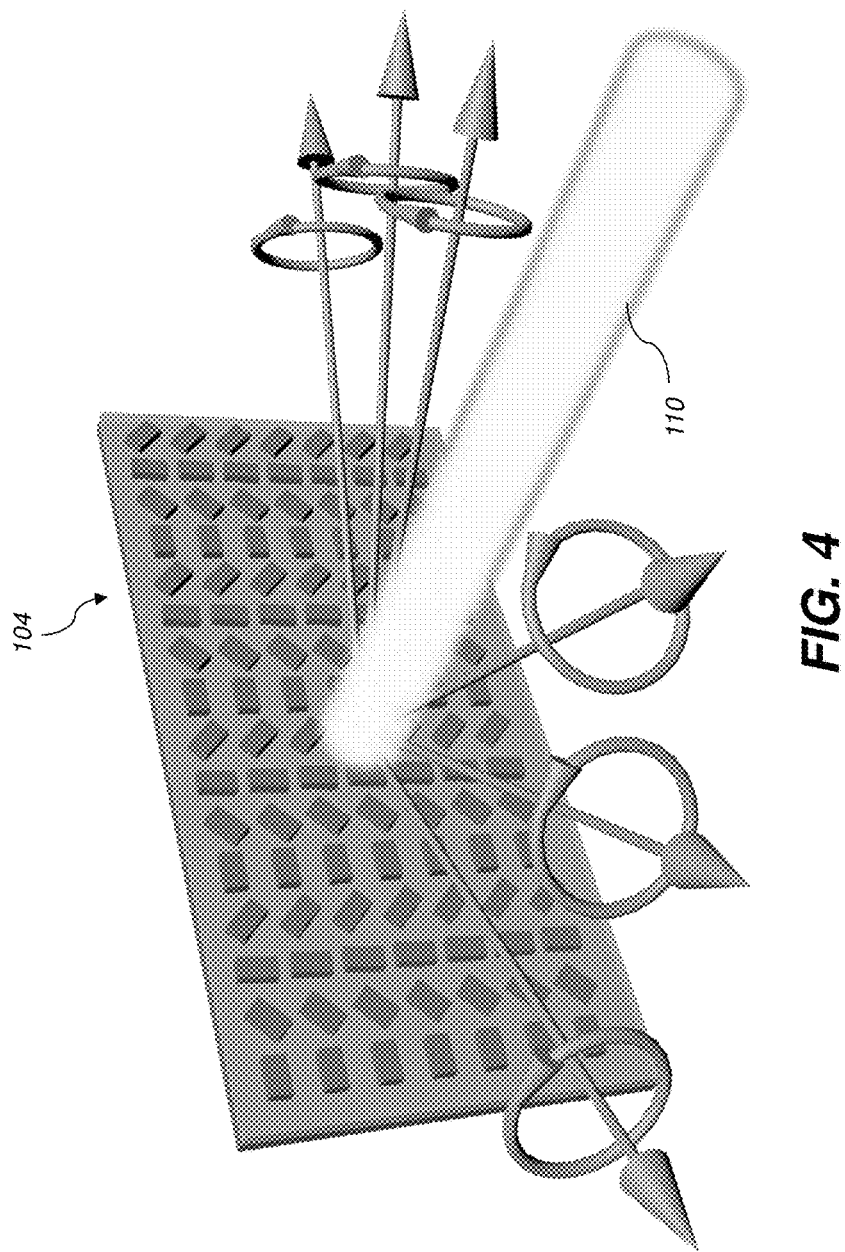
FIG. 4 shows a 3D schematic of the reflecting metasurface structure showing the direction of the light beam and the reflected LCP and RCP spectral light components according to one embodiment.
Figure 5:
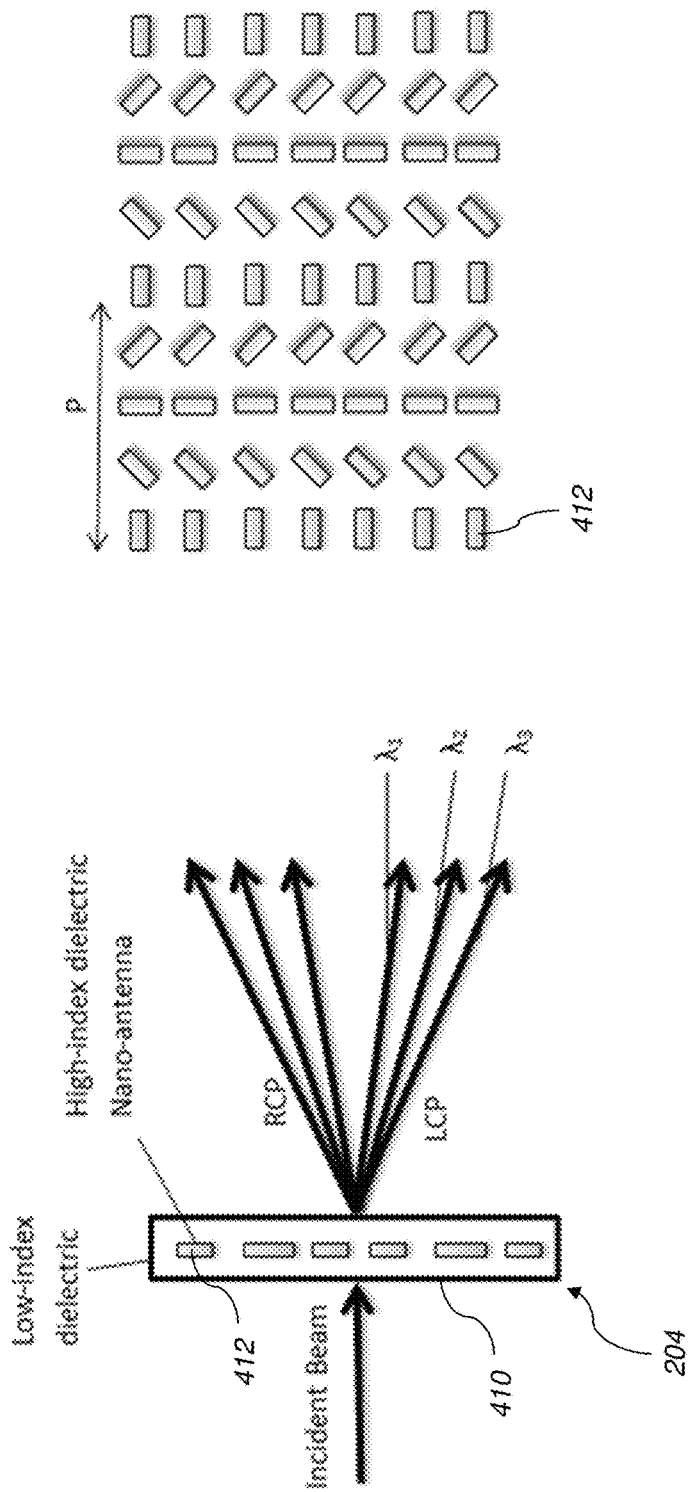
FIGS. 5(A) and 5(B) show the structure of the transmission metasurface of FIG. 2 from a cross-sectional view and a top view, respectively, according to one embodiment.

The reflecting metasurface 104 as shown in FIGS. 3 and 4 comprises three layers: (1) a backward reflecting metal layer 308; (2) an intermediate dielectric spacer layer 310; (3) an antenna array layer 311 comprising an array of metallic nano-antennas 312. The reflecting metal layer 308 may be implemented using any metal, including but not limited to gold, silver, copper, aluminum, titanium nitride, and zirconium nitride. The thickness of the layer 308 can be in the range of 10 nanometers up to a 500 nanometers. The layer 308 can be grown using any chemical vapor deposition (CVD) or physical vapor deposition (PVD) technologies known in the art. The spacer layer 310 may be composed of a dielectric material, including but not limited to silica, alumina, and PMMA, and is in the range of 10-100 nanometers in thickness. Spacer layer 310 can also be fabricated using any chemical vapor deposition (CVD) or physical vapor deposition (PVD) technologies known in the art. In certain embodiments, the antenna array layer 311 may comprise any metal, including but not limited to gold, silver, copper, aluminum, titanium nitride, zirconium nitride. In other embodiments, the antenna array layer 311 may comprise a plasmonic ceramic or transparent conducting oxide, including but not limited to aluminum doped zinc oxide (AZO) and gallium doped zinc oxide (GZO). The antenna array layer may be in the range of 10 to 100 nanometers in thickness. The antennas 312 may be fabricated, for example, using electron beam lithography or photo-lithography. The antennas 312 are preferably plasmonic. Each antenna 312 is preferably anisotropic in shape (e.g., rectangular), and it is preferable that the reflection coefficient across the major and minor axis be out of phase. This is achieved through adjusting the lateral dimensions of the antennas 312. The dimension selection depends on the wavelength of interest and the materials used. For near infra-red applications, dimensions in the order of 100-300 nm are suitable. Going towards shorter wavelengths, it is suitable to use silver nano-antennas of lateral dimensions in the order of tens of nanometers (e.g., 10-100 nanometers), and if aluminum is used, it is possible to go to ultraviolet wavelengths. Higher wavelengths (mid and far infra-red) can also be achieved by increasing the dimensions of the nano-antenna to few micrometers.

FIG. 3(A) shows a cross-sectional view of the metasurface 104 with a conceptual illustration of beam splitting of LCP and RCP components in different directions at a wavelength dependent angle λ. FIG. 3(B) shows a top view of the metallic nano-antenna array 311 portion of the metasurface 104. FIG. 4 shows a 3D schematic of the reflecting metasurface 104. The array 311 comprises a periodic structure of nano-antennas 312 (a period P of 4 antennas is shown in the illustrated embodiment). For each period P, the major axes of the antennas are oriented at different angles with respect to each other to span 180 degree orientation across the period. For the case of a 4 antenna period, the orientation angles of the axes are 0, 45°, 90° and 135°. Across each period, the nano-antennas 312 form a phase distribution from 0 to $2\pi$ ($-2\pi$) for reflected LCP (RCP) beam. This causes the reflected beam not to be normally reflected, but instead, reflected at an angle $\theta_r$ defined $\sin \theta_r = \lambda/P$ for LCP and $\sin \theta_r = -\lambda/P$ for RCP, where λ is the wavelength and P is the period. This explains the spatial separation of LCP and RCP and wavelength dependence of the reflection angle. The period P must be designed to be larger than any wavelength λ, in our operating band because the equation $\sin \theta_r = \lambda/P$ implies that $\lambda/P < 1$.

FIG. 5(A) shows the schematics of the transmission metasurface 204. It comprises an array of high-index nano-antennas 412 embedded inside a low-index medium 410. The antennas 412 are preferably plasmonic. The metasurface 204 may be fabricated layer by layer, where a layer of low-index medium (e.g., silica, alumina, or PMMA) is deposited using any of the chemical vapor deposition (CVD) or physical vapor deposition (PVD) technologies. This can be in the range of 10-1000 nanometers in thickness. Then the array of high-index dielectric (e.g., silicon, germanium) is patterned using electron beam lithography or photo-lithography. The top view of the pattern is shown in FIG. 5(B). Then low-index dielectric is deposited again to fill the space between the nano-antennas 412 and to build some thickness on top of the array (e.g. in the range of 10-1000 nanometers). The thickness of the nano-antennas 412 is in the range of 100-1000 nanometers, and so are the lateral dimensions. The nano-antennas 412 are oriented the same way as the reflecting metasurface 104 metallic array. Similarly, the high-index dielectric nano-antennas 412 are anisotropic and their dimensions are adjusted such that the transmissions along the major and minor axes are out of phase. By similar analysis to that of the reflecting metasurface 104, the transmission angle $\theta_t$ follows the formula $\sin \theta_t = \lambda/P$ for LCP and $\sin \theta_t = -\lambda/P$ for RCP, where λ is the wavelength and P is the period. This explains the spatial separation of LCP and RCP and wavelength dependence of the transmission angle.

The incident light beam applied to the reflection metasurface 104 or transmission metasurface 204 need not be generated from a laser source. Any non-coherent source such as a lamp, a light emitting diode (LED), or a Xenon lamp maybe be used which has equal components of LCP and RCP which may be spatially separated by the metasurface 104 or 204.

Figure 6:
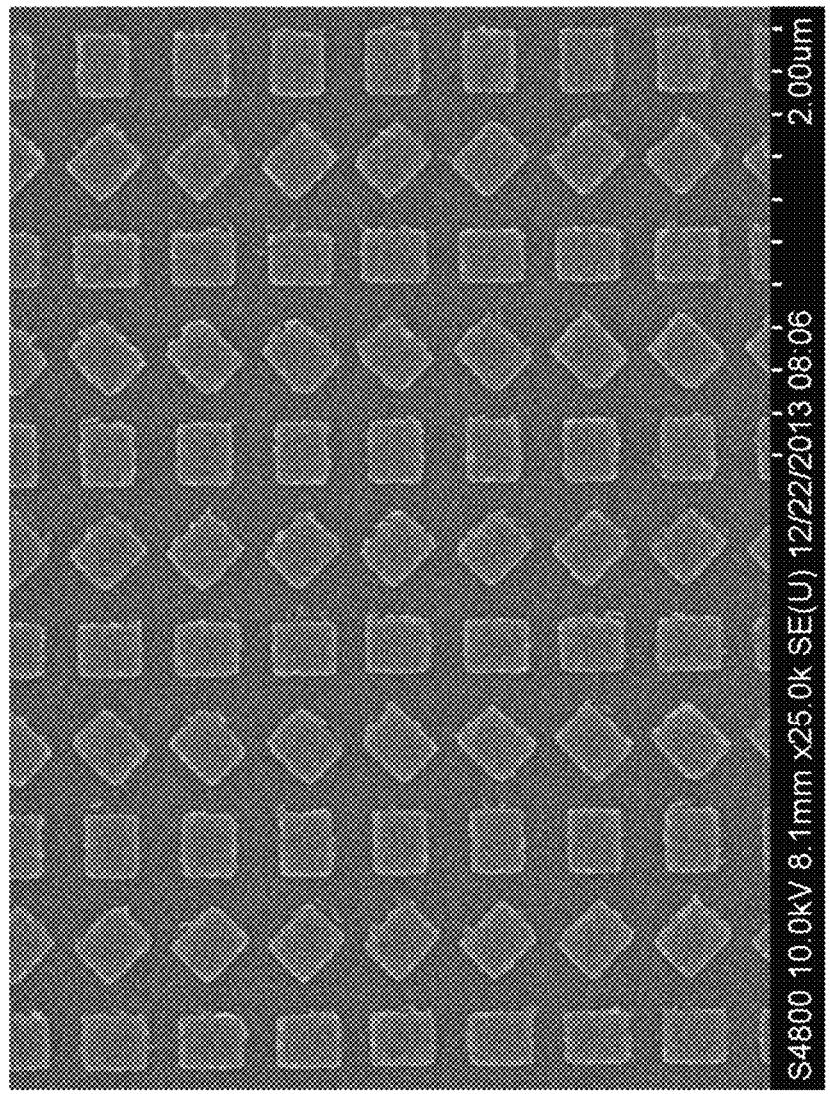
FIG. 6 shows an image of a fabricated reflecting metasurface according to one embodiment.

As a proof of feasibility, a reflecting metasurface was fabricated as shown in FIG. 6, with a bottom 50-nm gold layer, on top of which a 50-nm alumina layer, and the outermost layer of a rectangular antenna array of gold of 30-nm thickness and lateral dimensions of 230 nm×280 nm. The separation between antennas is 450 nm. The bottom gold and alumina layers are grown using electron beam deposition (one type of PVD), and then the nano-antenna arrays are fabricated using electron beam lithography. FIG. 6 shows a top FE SEM image of the fabricated metasurface.

Figure 7A:
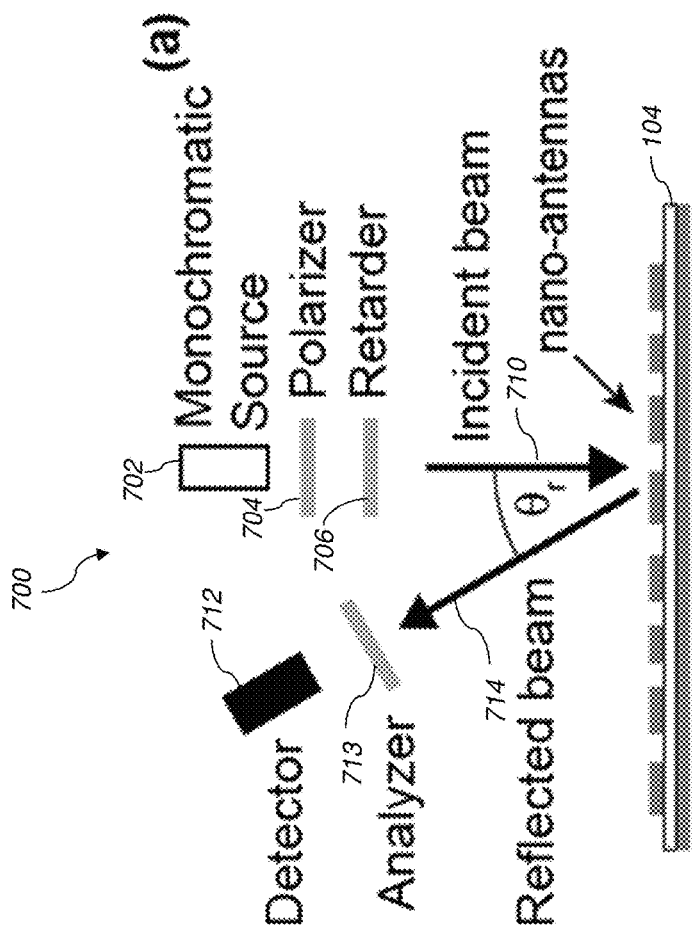
FIG. 7(A) shows a schematic of a system 700 used to test the fabricated sample in FIGS. 5(A) and 5(B).
Figure 7B:
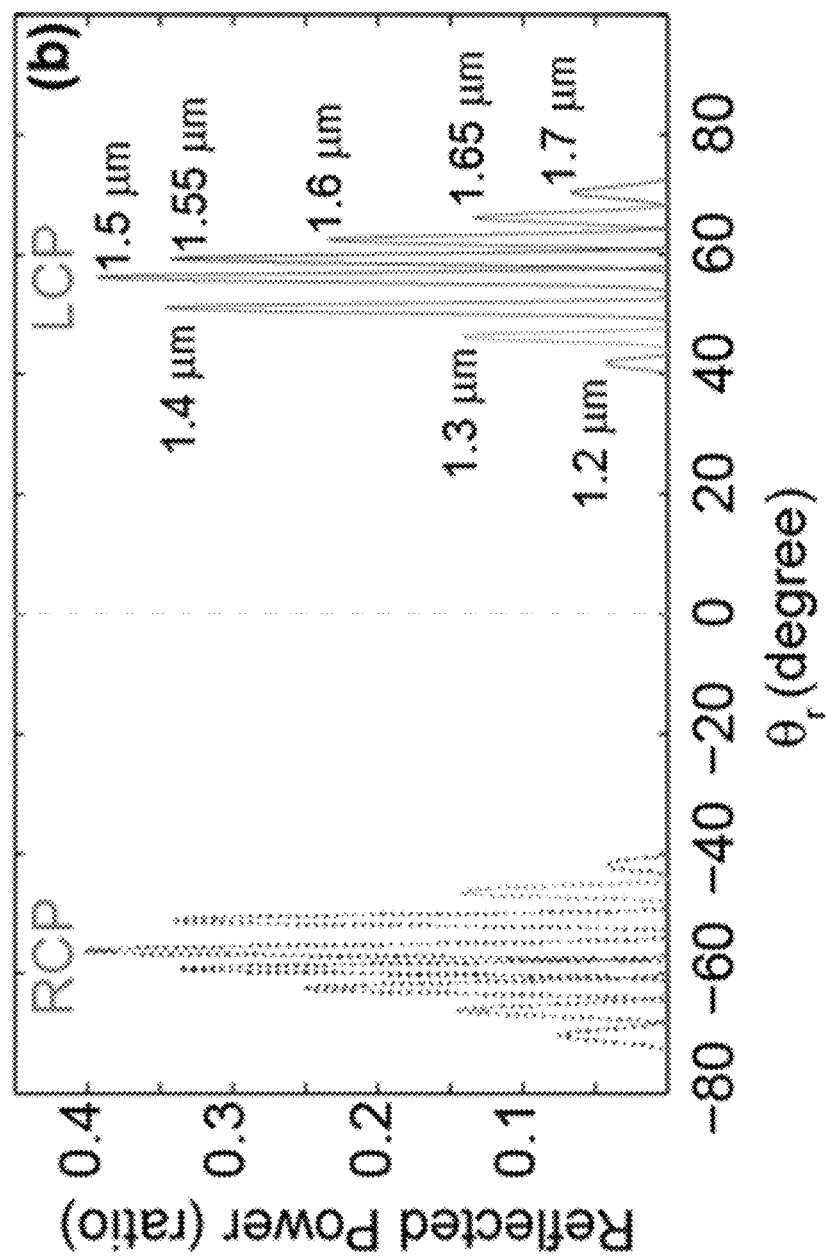
FIG. 7(B) shows experimental results of reflected power for LCP and RCP incident beams at different wavelengths as a function of reflected angle showing discrimination of LCP and RCP spectra according to one embodiment.
Figure 8:
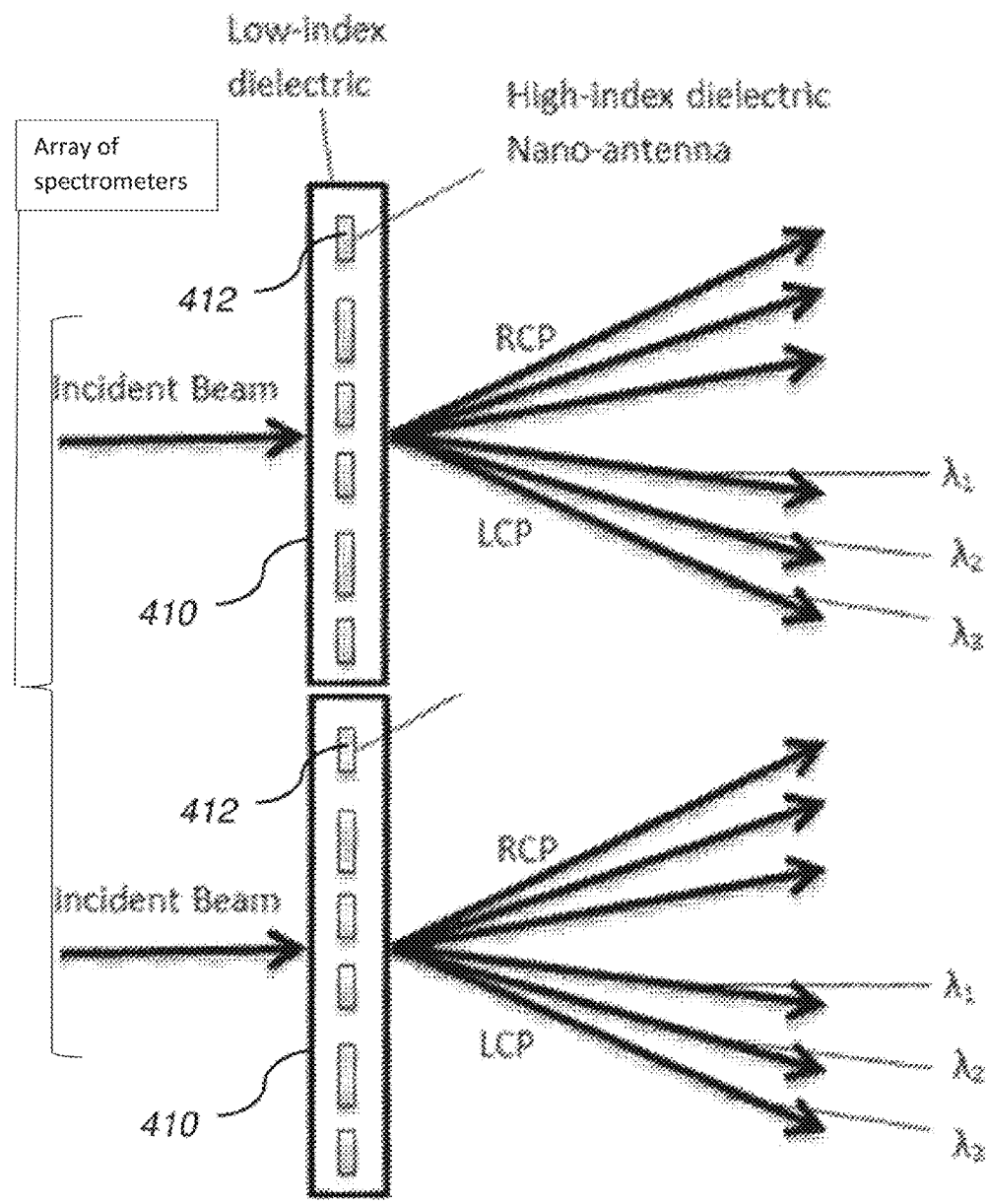
FIG. 8 illustrates a CD spectrometer in accordance with one or more embodiments.

FIG. 7(A) shows a schematic of a system 700 used to test the fabricated sample in FIGS. 5(A) and 5(B). The system 700 comprises a tunable monochromatic source 702, a polarizer 704, and a retarder 706 which are utilized to obtain circularly polarized incident beams 710 for different wavelengths. Measurements are taken using a rotating arm device (e.g., with an optional analyzer 713) which allows rotation of a detector 712 to collect the reflected beam 714 as a function of reflection angle $\theta_r$. FIG. 7(B) shows experimental results of reflected power for LCP and RCP incident beams at different wavelengths as a function of reflected angle showing discrimination of LCP and RCP spectra. LCP is reflected at the right side, and RCP is reflected at the left side. Wavelengths varying in the range 1.2-1.7 µm are reflected at different angles (40°-70°) with RCP reflection angles being mirror images of LCP reflection angles. Power efficiency of up to 40% is demonstrated. Efficient discrimination of LCP and RCP spectra is verified.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into the processor (and possibly also other processors), to cause functions, acts, or operational steps of various aspects herein to be performed by the processor. Computer program code for carrying out operations for various aspects described herein may be written in any combination of one or more programming language(s).

The invention is inclusive of combinations of the aspects described herein. References to "a particular aspect" or "embodiment" and the like refer to features that are present in at least one aspect of the invention. Separate references to "an aspect" (or "embodiment") or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

What is claimed is:

1. A circular dichroism spectrometer, comprising:
    a metasurface, the metasurface having a plurality of anisotropic antennas configured to simultaneously spatially separate LCP and RCP spectral components from an incoming light beam; and
    an optical detector array, the array configured to detect the LCP and RCP spectral components.

2. The spectrometer according to claim 1, further comprising a transparent medium disposed between the metasurface and the optical detector array.

3. The spectrometer according to claim 1, wherein the overall dimensions of the spectrometer are each less than 1 millimeter.

4. The spectrometer according to claim 1, further comprising a light source for generating the incoming light beam.

5. The spectrometer according to claim 4, wherein the light source comprises an LED or Xenon lamp.

6. The spectrometer according to claim 1, wherein the metasurface is configured to operate in a reflection mode.

7. The spectrometer according to claim 1, wherein the metasurface is configured to operate in a transmission mode.

8. The spectrometer according to claim 1, wherein the antennas comprise a dielectric material.

9. The spectrometer according to claim 1, wherein the antennas comprise a metallic material.

10. The spectrometer according to claim 1, wherein the antennas comprise a plasmonic ceramic material.

11. The spectrometer according to claim 1, wherein the antennas comprise a transparent conducting oxide material.

12. The spectrometer according to claim 1, wherein the antennas comprise a rectangle, ellipse, or split-ring shape.

13. The spectrometer according to claim 1, wherein the antennas comprise solid nano-particles.

14. The spectrometer according to claim 1, wherein the antennas comprise nano-slits.

15. The spectrometer according to claim 1, wherein the antennas comprise nano-holes.

16. The spectrometer according to claim 1, wherein the metasurface is adjustable to work at multiple wavelength ranges, including ultraviolet, visible, and infrared.

17. The spectrometer according to claim 1, wherein the spectrometer is configured to capture biological data.

18. The spectrometer according to claim 1, wherein the spectrometer is configured to capture data for DNA structural analysis.

19. The spectrometer according to claim 1, wherein the spectrometer is configured to capture stereochemical data.

20. The spectrometer according to claim 1, wherein the spectrometer is configured to capture crystallography data.

21. A sensor network, comprising:
    an array of spectrometers, each of the spectrometers comprising:
        a metasurface, the metasurface having a plurality of anisotropic antennas configured to simultaneously spatially separate LCP and RCP spectral components from an incoming light beam; and
        an optical detector array, the array configured to detect the LCP and RCP spectral components.

* * * * *